US00PP21017P3

(12) United States Plant Patent
Hanna et al.

(10) Patent No.: US PP21,017 P3
(45) Date of Patent: May 25, 2010

(54) BERMUDAGRASS 'ST-5'
(50) Latin Name: *Cynodon transvaalensis×Cynodon dactylon*
Varietal Denomination: ST-5

(75) Inventors: Wayne William Hanna, Chula, GA (US); S. Kristine Braman, Griffin, GA (US)

(73) Assignee: University of Georgia Research Foundation, Athens, GA (US)

( * ) Notice: Subject to any disclaimer, the term of this patent is extended or adjusted under 35 U.S.C. 154(b) by 0 days.

(21) Appl. No.: 12/228,997

(22) Filed: Aug. 19, 2008

(65) Prior Publication Data

US 2010/0050306 P1 Feb. 25, 2010

(51) Int. Cl.
*A01H 5/00* (2006.01)

(52) U.S. Cl. ..... Plt./389

(58) Field of Classification Search ..... Plt./389
See application file for complete search history.

*Primary Examiner*—Annette H Para
(74) *Attorney, Agent, or Firm*—Davis Wright Tremaine LLP

(57) ABSTRACT

Bermudagrass 'ST-5' is provided. The new and distinct dwarf variety has excellent shade tolerance, superior tawny mole cricket non-preference, small seed heads, and thrives in hot and humid conditions. The asexually reproduced triploid variety is reliably propagated vegetatively.

5 Drawing Sheets

Latin name: Bermudagrass 'ST-5' is an inter-specific hybrid of the genus and species *Cynodon transvaalensis*× *Cynodon dactylon.*

Variety denomination: The new bermudagrass claimed is of the variety denominated 'ST-5.'

BACKGROUND OF THE INVENTION

The present invention relates to a new and distinct cultivar of bermudagrass botanically known as *Cynodon transvaalensis*×*Cynodon dactylon*, and herein referred to as 'ST-5.'

The new bermudagrass is a product of a planned breeding program conducted by the Inventors in Tifton, Ga. The objective of the bermudagrass breeding program is to create new plant cultivars with improved commercial qualities. This cultivar is commercially important for its superior shade tolerance and other qualities, which are enumerated herein.

Pedigree and history: Several *C. transvaalensis* parents (unpatented) were crossed with several *C. dactylon* parents (unpatented) in Tifton, Ga. Crosses were made in the field by surrounding each *C. transvaalensis* parent with a *C. dactylon* parent in 6-feet square plots. All crosses were in close proximity, and resulted in somewhat random parentage of all resulting progeny. Progenies were planted from the cross combinations. Once established, the plots were mowed three times per week at one-fourth inch height setting on the mower. Plants that maintained density, color, and tawny mole cricket non-preference were selected in the fall of the second year after planting. One selection, 'ST-5' (ST for shade tolerant), was identified as a nice dwarf and tested for nine years in three field (full sun) and three shade tests in Tifton, Ga. Bermudagrass 'ST-5' was also tested for insect resistance in Tifton, Ga.

Asexual reproduction of the new bermudagrass by vegetative terminal cuttings in a controlled environment in Tifton, Ga., since 1993, has shown that the unique features of this new bermudagrass are stable and reproduced true to type in successive generations.

SUMMARY OF THE INVENTION

The cultivar 'ST-5' has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'ST-5':

1. Excellent shade tolerance;
2. Superior tawny mole cricket non-preference;
3. Dwarf;
4. Small seed head;
5. High seed head number; and
6. Thrives in hot and humid conditions.

The present bermudagrass 'ST-5' may be compared to other grasses developed by researchers, such as that with the commercial names (unpatented, unregistered trademarks): 'Tifdwarf,' 'Tifgreen,' 'TifSport,' and 'Tifway.'

Some data are by means of multi-ratings. In Tifton, Ga. ratings were taken monthly from April to October. No insecticides, fungicides or herbicides except for one pound per acre of atrazine in March were used in generating the data. The "turf quality" rating is a general rating wherein density, color, texture, pest resistance are considered for evaluating the desirability of the turf.

Comparison to 'TifSport'. 'ST-5' most closely resembles 'TifSport.' 'ST-5' has significantly more shade tolerance than 'TifSport,' especially after the first year of establishment. Turf quality is as good or better than 'TifSport.' Plant color for 'ST-5' is as good or better than 'TifSport.' In most years, 'ST-5' tends to produce significantly more seed heads than 'TifSport,' and has similar rhizome size and density. In field plots where other grass cultivar/genotypes are present, 'ST-5' has significantly better tawny mole cricket non-preference than 'TifSport.' However, in greenhouse studies under non-preference, 'ST-5' had higher mole cricket reproduction values than 'TifSport.' 'ST-5' has similar resistance to the two-lined spittle bug and army worm as 'TifSport.' Other comparisons are shown in Table 1.

TABLE 1

Summary of morphological characteristics of 'ST-5' and 'TifSport.'

| | Mean (mm) raceme length | Number of racemes per inflorescence Year | Height (cm) ground to top of inflorescence |
|---|---|---|---|
| Cultivar | 2006 | 2006 | 2006 |
| 'ST-5' | 20.49 | 2.39 | 14.224 |
| 'TifSport' | 25.24 | 2.75 | 17.569 |
| LSD-5% | 0.84 | 0.16 | 1.1 |

| | Height (cm) ground to top of leaves | Mean leaf length (mm) Year | Mean leaf width (mm) |
|---|---|---|---|
| Cultivar | 2006 | 2007 | 2007 |
| 'ST-5' | 8.56 | 30.24 | 1.51 |
| 'TifSport' | 12.58 | 38.24 | 1.73 |
| LSD-5% | 0.86 | 4.45 | 0.09 |

Note:
Leaf measurements were taken at the third node from the apical meristem.

Comparison to 'Tifdwarf.' Bermudagrass 'ST-5' is a darker green, has more tawny mole cricket non-preference, and is more dense than 'Tifdwarf.'' ST-5' has similar resistance to the two-lined spittle bug and army worm as 'Tifdwarf,' but less resistance to the bermudagrass mite.

Comparison to 'Tifgreen.' Bermudagrass 'ST-5' is a darker green and more dense than 'Tifgreen.'

Comparison to 'Tifway.' 'ST-5' has significantly more shade tolerance than 'Tifway,' especially after the first year of establishment. Turf quality is as good or better than 'Tifway.' Plant color for 'ST-5' is as good or better than 'Tifway.' In most years, 'ST-5' tends to produce significantly more seed heads than 'Tifway.' In field plots where other grass cultivar/genotypes are present, 'ST-5' has significantly better tawny mole cricket non-preference than 'Tifway.' However, in greenhouse studies under non-preference, 'ST-5' had higher mole cricket reproduction values than did 'Tifway.' 'ST-5' has similar resistance to the two-lined spittle bug and army worm as 'Tifway,' less resistance to the bermudagrass mite.

Comparison to Parents. 'ST-5' is, for the most part, intermediate in characteristics to its parents. 'ST-5' has the fine leaf and stem texture of the female parent, *C. transvaalensis*, and the darker green leaf color, rhizomes, persistence, and toughness of the male parent (*C. dactylon*). Rhizome development is intermediate to that of *Cynodon transvaalensis* (which has no rhizomes) and *Cynodon dactylon* (which has large, vigorous rhizomes). The inflorescence of 'ST-5' is a panicle. In addition, the stigmas are red-purple 59B and the anthers are a grayed-orange 173a based on The Royal Horticultural Society Colour Chart, $5^{th}$ ed.. The anthers are spongy and non-dehiscent due to the sterility typical of triploids.

BOTANICAL DESCRIPTION

Figure 1:
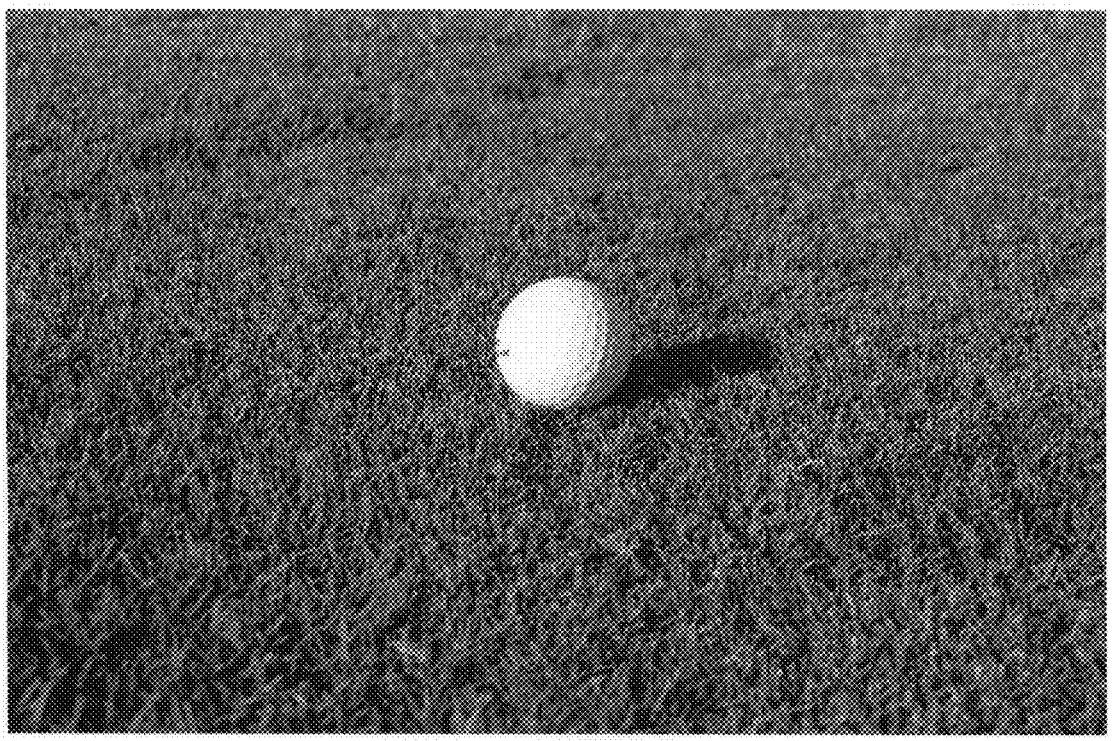
FIG. 1 is a photograph of the shade tolerant bermudagrass 'ST-5' with a golf ball for size comparison.
Figure 2:
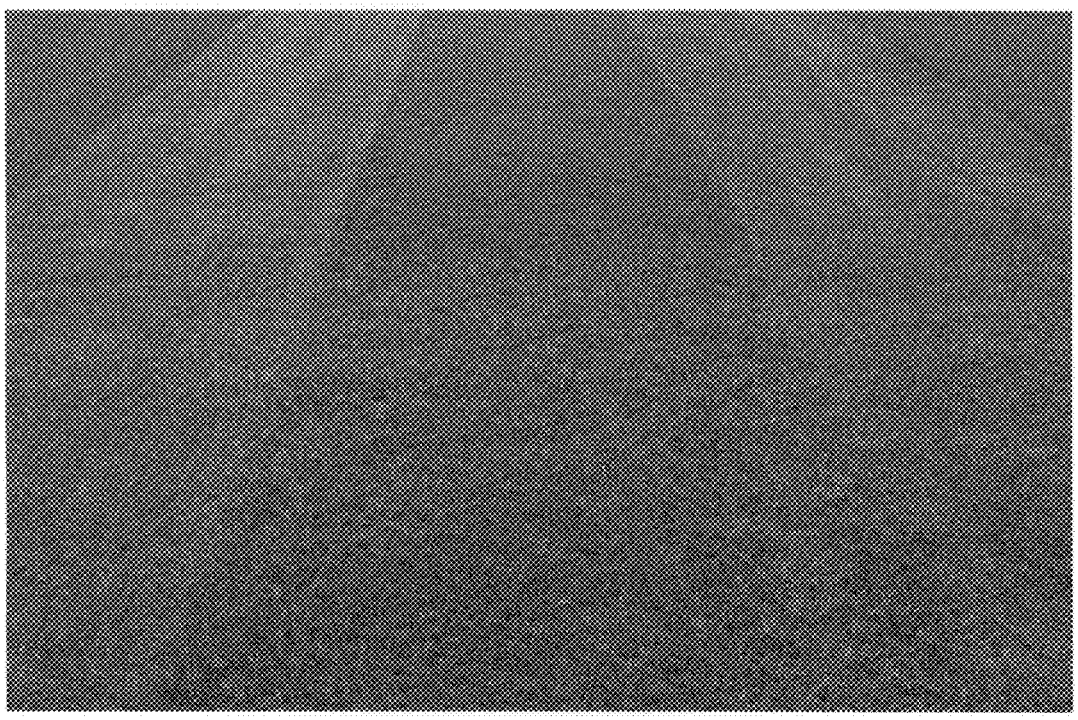
FIG. 2 is a photograph of an expanse of 'ST-5'.
Figure 3:
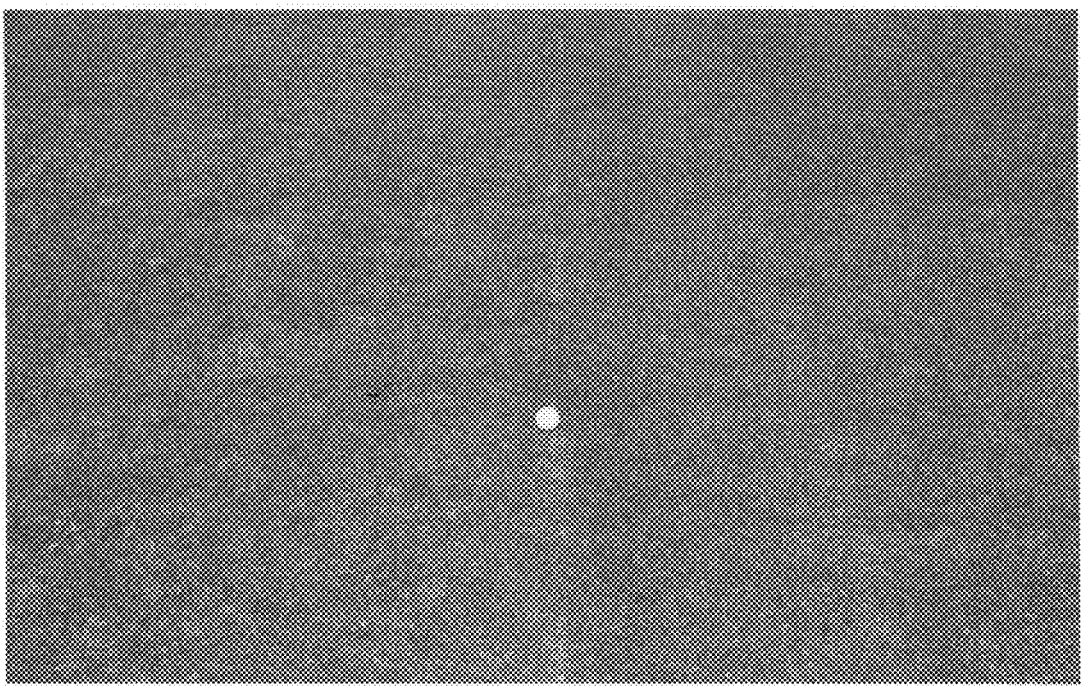
FIG. 3 is a photograph of two grasses grown for three years in 70% shade, with 'Tifway' on the left and 'ST-5' on the right.
Figure 4:
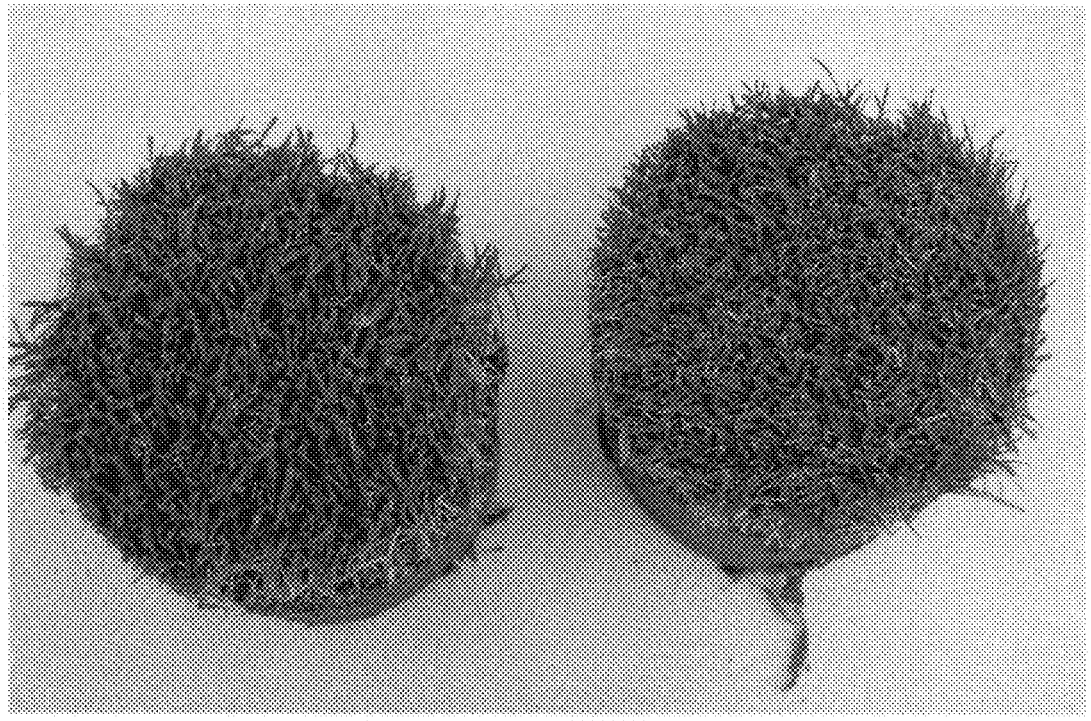
FIG. 4 is a photograph of two grass plugs, with a plug of 'TifSport' on the left and a plug of 'ST-5' on the right.
Figure 5:
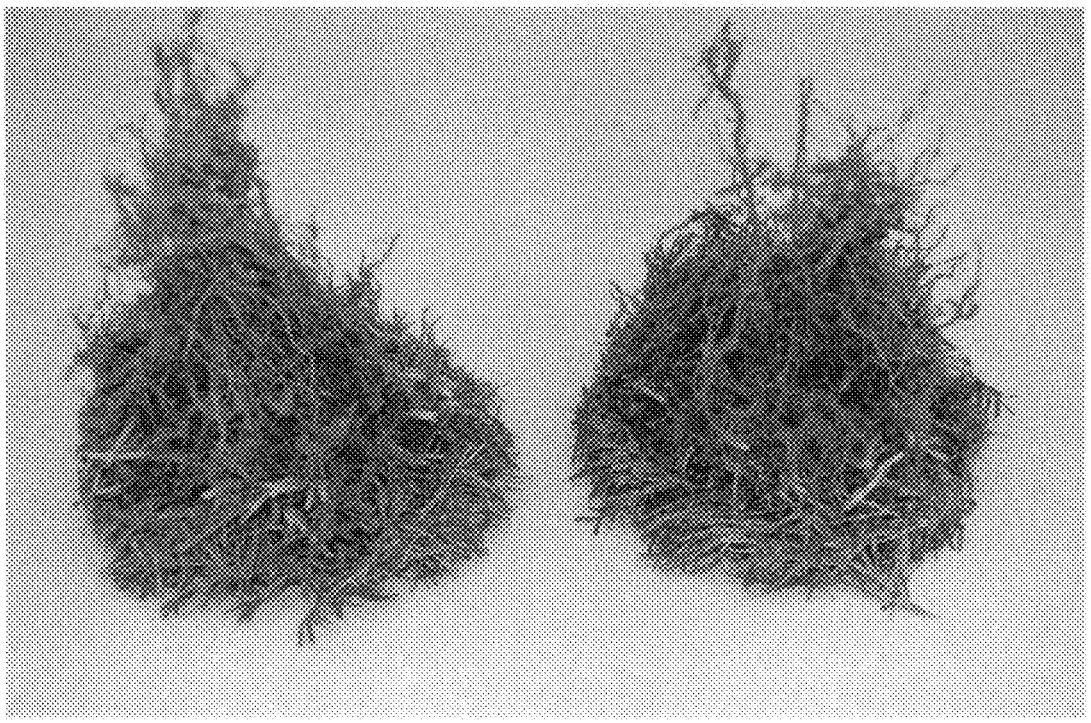
FIG. 5 is a photograph of two grass plugs, with the roots and rhizomes of 'TifSport' as shown on the left and 'ST-5'.

The following observations, measurements and values describe plants grown in Tifton, Ga., by Wayne Hanna and Kristine Braman. During the growing of the plants, day temperatures ranges from 69° F. to 99° F. and night temperatures ranges from 47° F. to 70° F. Plants were mowed at one fourth to one half inch height. Approximately two year old sod was mowed at 25 mm height once per week. 'ST-5' was fertilized with about 1 pound of nitrogen per month.

'ST-5' has leaf color which most fits the Green Group 138B of The Royal Horticultural Society (R.H.S.) Colour Chart, 5th Edition. 'ST-5' is a triploid hybrid, and does not produce seed or pollen, despite the fact that it produces more seed heads than some varieties. It is vegetatively propagated, ordinarily by sprigs or sod.

In addition to the data provided in the Summary of the Invention, bermudagrass 'ST-5' produces a small seed head on a thin peduncle in late May and June, which is typical of bermudagrasses in general, but 'ST-5' produces slightly more seed heads than desired, which is the only negative trait of this cultivar. A management solution is available to address this issue; treatment with a commercial product PrimoMAXX® will effect a reduction in number of seed heads. The bermudagrass mite is mainly a problem on stressed grass; it is possible to overcome this problem via proper management.

Additionally, 'ST-5' has been growing in non-replicated shade situations. It has performed well where the shade is not more than 70%. If shade presence is greater than 70% shade, 'ST-5' will maintain a turf, but it will thin out as the shade increases. At 95% shade, 'ST-5' will rate a 3–4 on a scale of 1–9 where 9 is best. 'Tifway' and 'TifSport' will not grow at 95% shade conditions. Moreover, a rating of 3 or 4 is enough sod to keep the soil from eroding, which is a desirable feature in addition to the aesthetic features seen in this cultivar.

The un-replicated plantings were: in residential lawns in Roswell, Ga., for 5 years; in the rough on a golf course in Mobile, Ala., for 3 years; in a residential lawn in Martinez, Ga., for 3 years; in the tee box at a golf course in Pinehurst, N.C., for 2 years; on the rough at a golf course in Atlanta, Ga., for 2 years; on the rough at a golf course in East Lake, Ga., for 2 years.

What is claimed is:

1. The new and distinct variety of the bermudagrass 'ST-5' plant as described and illustrated herein.

* * * * *